US012560521B2

(12) United States Patent
Liu et al.

(10) Patent No.: US 12,560,521 B2
(45) Date of Patent: Feb. 24, 2026

(54) DETERMINING INITIAL PORE PRESSURE

(71) Applicant: Saudi Arabian Oil Company, Dhahran (SA)

(72) Inventors: Hui-Hai Liu, Houston, TX (US); Jilin Jay Zhang, Houston, TX (US); Rabah Mesdour, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 314 days.

(21) Appl. No.: 18/382,011

(22) Filed: Oct. 19, 2023

(65) Prior Publication Data

US 2025/0130154 A1 Apr. 24, 2025

(51) Int. Cl.
  *G01N 15/08* (2006.01)
  *G01N 33/24* (2006.01)

(52) U.S. Cl.
  CPC ......... *G01N 15/0826* (2013.01); *G01N 33/24* (2013.01)

(58) Field of Classification Search
  CPC .... G01N 15/00; G01N 15/08; G01N 15/0826; G01N 33/24
  See application file for complete search history.

(56) References Cited

U.S. PATENT DOCUMENTS

| | | | |
|---|---|---|---|
| 4,193,451 A | 3/1980 | Dauphine | |
| 4,345,650 A | 8/1982 | Wesley | |
| 6,871,532 B2 * | 3/2005 | Zazovsky | ............... E21B 47/06 73/152.01 |
| 6,968,274 B2 * | 11/2005 | Tutuncu | ................ E21B 49/005 702/14 |
| 9,746,410 B2 | 8/2017 | Chertov et al. | |
| 9,896,919 B1 | 2/2018 | Chen et al. | |
| 9,983,106 B2 | 5/2018 | Han et al. | |
| 10,048,179 B2 | 8/2018 | Lai et al. | |
| 10,180,054 B2 | 1/2019 | Chen et al. | |
| 10,254,207 B2 | 4/2019 | Lai et al. | |
| 10,401,274 B2 | 9/2019 | Liu et al. | |
| 10,415,358 B2 | 9/2019 | Lai et al. | |
| 10,416,064 B2 | 9/2019 | Chen et al. | |
| 10,443,367 B2 | 10/2019 | Chen et al. | |
| 10,571,384 B2 | 2/2020 | Liu et al. | |
| 10,669,829 B2 | 6/2020 | Liang | |

(Continued)

FOREIGN PATENT DOCUMENTS

| | | | |
|---|---|---|---|
| CN | 111999227 A * | 11/2020 | ......... G01N 15/0826 |
| WO | WO 2021053193 | 3/2021 | |

OTHER PUBLICATIONS

Machine Translation of CN-111999227-A (Year: 2020).*

(Continued)

*Primary Examiner* — Nguyen Q. Ha

(74) *Attorney, Agent, or Firm* — Fish & Richardson P.C.

(57) ABSTRACT

A method includes performing, on a core sample obtained from a reservoir and positioned in a permeability measurement assembly that includes a flow inlet, a permeability operation by flowing a test fluid from the flow inlet and into the core sample and changing an effective stress acting on the core sample. The method also includes determining a natural logarithm of permeability of the core sample as a function of the effective stress, and determining, as a function of the natural logarithm of permeability of the core sample, an initial pore pressure of the reservoir.

20 Claims, 4 Drawing Sheets

(56) References Cited

U.S. PATENT DOCUMENTS

| 10,760,395 B2 | 9/2020 | Lai et al. |
|---|---|---|
| 10,760,396 B2 | 9/2020 | Chen et al. |
| 10,801,943 B2 | 10/2020 | Yue et al. |
| 10,845,292 B2 | 11/2020 | Georgi |
| 10,858,936 B2 | 12/2020 | Chen et al. |
| 10,920,556 B2 | 2/2021 | Chen et al. |
| 11,248,446 B2 | 2/2022 | Liang et al. |
| 11,530,972 B2 | 12/2022 | Liu et al. |
| 11,598,711 B2 | 3/2023 | Liu et al. |
| 11,643,924 B2 | 5/2023 | Zhang |
| 11,680,887 B1 | 6/2023 | Zhang et al. |
| 2008/0216559 A1 | 9/2008 | Hilab |
| 2019/0309611 A1 | 10/2019 | Liang et al. |
| 2019/0353575 A1 | 11/2019 | Clarkson et al. |
| 2020/0363310 A1 | 11/2020 | Zhang et al. |
| 2022/0112422 A1 | 4/2022 | Liang et al. |
| 2022/0214261 A1 | 7/2022 | Liu et al. |
| 2022/0214262 A1 | 7/2022 | Liu et al. |
| 2022/0397034 A1* | 12/2022 | Alvarez ................. G01V 1/303 |

OTHER PUBLICATIONS

APMonitor.com [online], "Proportional integral derivative (PID)," Sep. 2020, retrieved Oct. 13, 2021, from URL<https://apmonitor.com/pdc/index.php/Main/ProportionalIntegralDerivative>, 6 pages.

Chen et al., "Dependence of gas shale fracture permeability on effective stress and reservoir pressure: Model match and insights, " Fuel, 2015, 139:383-392, 10 pages.

Civan et al., "Comparison of shale permeability to gas determined by pressure-pulse transmission testing of core plugs and crushed samples," Unconventional Resources Technology Conference, Jul. 2015, 11 pages.

Clarkson et al., "Use of pressure- and rate-transient techniques for analyzing core permeability tests for unconventional reservoirs: Part 2," SPE Unconventional Resources Conference, Nov. 2013, 14 pages.

Hildebrand et al., "DFIT Analysis and Simulation: A Utica Shale Field Study," SPE-201413-MS, SPE Annual Technical Conference & Exhibition originally scheduled to be held in Denver, Colorado, United States, Oct. 5-7, 2020, 20 pages.

Jones, "A Technique for Faster Pulse-Decay Permeability Measurements in Tight Rocks," SPE-28450-PA, SPE Reservoir Evaluation & Engineering, Mar. 1997, 12(1):19-25, 7 pages.

Karimi et al., "Formula of definite point overburden pressure of reservoir layers," Egyptian Journal of Petroleum, Jun. 2014, 23(2):175-182, 8 pages.

Liu et al., "Correction of source-rock permeability measurements owing to slip flow and Knudsen diffusion: a method and its evaluation," Petroleum Science, Dec. 2017, 15(1):116-125, 10 pages.

Metarocklab.com [online], "Pumps," 2019, retrieved Oct. 13, 2021, from URL<https://www.metarocklab.com/product-page/pressure-generators>, 2 pages.

Paroscientific.com [online], "Overview & product selection guide," Jan. 28, 2017, via Internet Archive: Wayback Machine URL <https://web.archive.org/web/20170128184102/https://paroscientific.com/products.php>, retrieved Oct. 13, 2021, URL<http://paroscientific.com/products.php>, 2 pages.

Tang et al., "Impact of Stress-Dependent Matrix and Fracture Properties on Shale Gas Production," Energies, Jul. 2017, 10(996):1-13, 13 pages.

U.S. Appl. No. 18/237,862, Liu et al., Systems and Methods for Enhancing Carbon Dioxide Injectivity Into a Subterranean Formation, filed on Aug. 24, 2023, 27 pages.

U.S. Appl. No. 18/382,011, Liu et al., Determining Initial Pore Pressure, filed Oct. 19, 2023, 28 pages.

U.S. Appl. No. 18/455,847, Liu et al., Caprock Analysis Methods and Systems, filed Aug. 25, 2023, 22 pages.

U.S. Appl. No. 18/481,731, Zhang et al., Determining Parameters of a Rock Sample, filed Oct. 5, 2023, 37 pages.

U.S. Appl. No. 18/598,383, Zhang et al., Measuring Rock Permeability, filed Mar. 7, 2024, 45 pages.

Zhang et al., "Matrix permeability measurement from fractured unconventional source-rock samples: Method and application," Journal of Contaminant Hydrology, Aug. 2020, 233(103663):1-6, 6 pages.

Zheng et al., "Relationships between permeability, porosity and effective stress for low-permeability sedimentary rock," International Journal of Rock Mechanics and Mining Sciences, 2015, 78:304-318, 15 pages.

* cited by examiner

Differential Stress

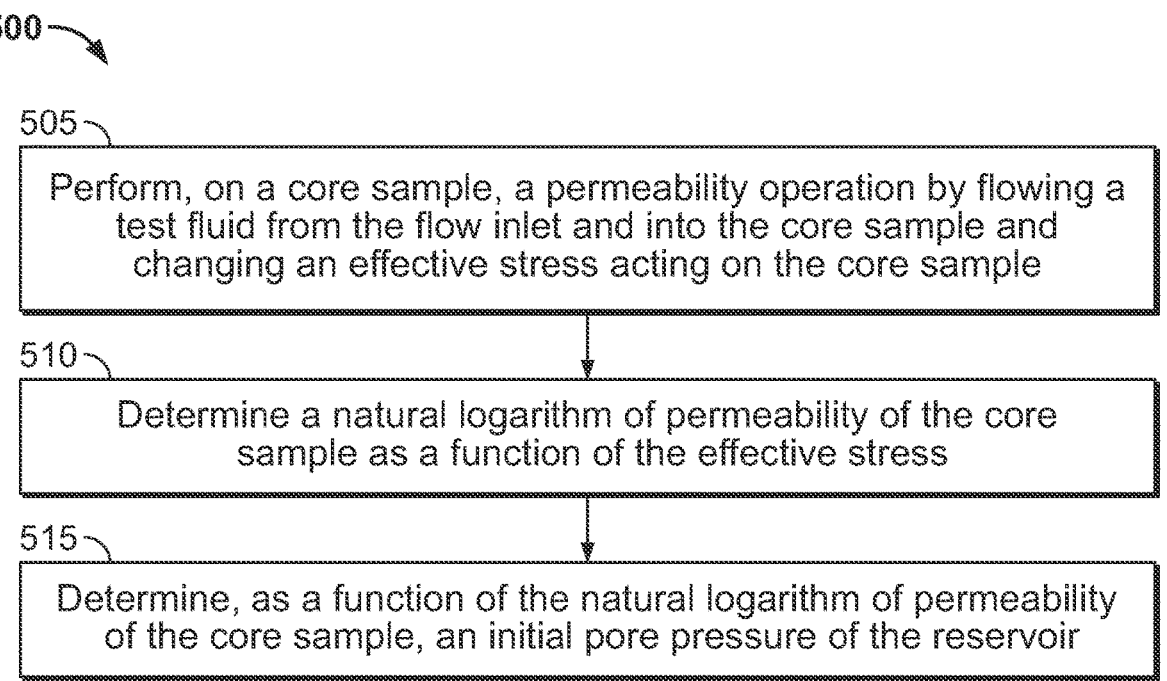

500

505
Perform, on a core sample, a permeability operation by flowing a test fluid from the flow inlet and into the core sample and changing an effective stress acting on the core sample 510
Determine a natural logarithm of permeability of the core sample as a function of the effective stress 515
Determine, as a function of the natural logarithm of permeability of the core sample, an initial pore pressure of the reservoir

FIG. 5

PROCESSOR
610

620

MEMORY

650

STORAGE
DEVICE
630

INPUT/OUTPUT

640
INPUT/
OUTPUT
DEVICES

DETERMINING INITIAL PORE PRESSURE

TECHNICAL FIELD

The present disclosure describes apparatus, systems, and methods for determining rock properties such as initial pore pressure.

BACKGROUND

Initial pore pressure in an unconventional reservoir is an important parameter for both reservoir characterization and development. The initial pore pressure is closely related to hydrocarbon in place. For the given pore spaces in a reservoir, a higher pore pressure gives a larger reservoir reserve. Furthermore, when other conditions remain the same, a higher initial pore pressure also results in a larger rate of hydrocarbon production from a production well. Methods and equipment to determine initial pore pressure are sought.

SUMMARY

Implementations of the present disclosure include a method that includes performing, on a core sample obtained from a reservoir and positioned in a permeability measurement assembly that includes a flow inlet, a permeability operation by flowing a test fluid from the flow inlet and into the core sample and changing an effective stress acting on the core sample. The method also includes determining a natural logarithm of permeability of the core sample as a function of the effective stress, and determining, as a function of the natural logarithm of permeability of the core sample, an initial pore pressure of the reservoir.

In some implementations, the method further includes, before determining the initial pore pressure of the reservoir, determining, as a function of the natural logarithm of permeability of the core sample, an initial effective stress of the core sample. Determining the initial pore pressure of the reservoir includes determining, as a function of the initial effective stress of the core sample, the initial pore pressure of the reservoir.

In some implementations, the initial effective stress of the core sample is a point of effective stress at which a rate of change of the natural logarithm of permeability increases.

In some implementations, determining the initial effective stress of the core sample includes generating a graph including an effective stress versus natural logarithm of permeability curve, and determining the initial effective stress of the core sample includes determining a point of effective stress in the graph in which a slope of the curve increases.

In some implementations, changing the effective stress includes increasing the effective stress from a first value of effective stress that is less than the initial effective stress of the reservoir, to a value of effective stress that is greater than the initial effective stress of the reservoir.

In some implementations, increasing the effective stress includes increasing a pressure of a confining fluid residing within a pressurized container in which the core sample resides during the permeability operation.

In some implementations, the initial effective stress of the reservoir is an initial effective stress of the core sample under reservoir conditions, and determining the initial pore pressure of the reservoir includes determining the initial pore pressure of the reservoir and a predetermined overburden stress of the reservoir.

In some implementations, determining the initial pore pressure of the reservoir includes first determining the overburden stress of the reservoir as a function of i) depth of the core sample, ii) ground surface pressure, iii) gravitational acceleration, and iv) a density of overlying rock, and then subtracting the initial effective stress of the core sample under reservoir conditions from the overburden stress of the reservoir.

In some implementations, performing the permeability operation includes using at least one of a steady-state flow method or a pressure pulse decay method.

In some implementations, the effective stress includes a pressure differential between a pore pressure of the core sample and a confining pressure exerted on the core sample by a confining fluid, and increasing the effective stress includes increasing the confining pressure while maintaining the pore pressure substantially constant.

Implementations of the present disclosure include a method that includes receiving, by a system that includes one or more computers in one or more locations, sensor feedback from one or more sensors of a core sample test assembly that includes a flow inlet and a flow outlet, the core sample test assembly containing a core sample obtained from a reservoir, and the receiving including receiving the sensors feedback while the core sample test assembly performs a permeability operation on the core sample by flowing a test fluid from the flow inlet, across the core sample, and out of the flow outlet. The method also includes determining, by the system and as a function of the sensor feedback, an effective stress acting on the core sample as the effective stress acting on the core sample increases. The method also includes determining, by the system, a natural logarithm of permeability of the core sample as a function of the effective stress, and determining, by the system and as a function of the natural logarithm of permeability of the core sample, an initial pore pressure of the reservoir.

In some implementations, the method further includes, before determining the initial pore pressure of the reservoir, determining, by the system and as a function of the natural logarithm of permeability of the core sample, an initial effective stress of the core sample. Determining the initial pore pressure of the reservoir includes determining, by the system and as a function of the initial effective stress of the core sample, the initial pore pressure of the sample.

In some implementations, the initial effective stress of the core sample is a point of effective stress at which a rate of change of the natural logarithm of permeability increases.

In some implementations, determining the initial effective stress of the core sample includes generating, by the system and on a user interface, a graph including an effective stress versus natural logarithm of permeability curve, and determining the initial effective stress of the core sample includes determining a point of effective stress in the graph in which a slope of the curve increases.

In some implementations, the initial effective stress of the core sample is an initial effective stress of the core sample under reservoir conditions, and determining the initial pore pressure of the reservoir includes determining, by the system, the initial pore pressure of the reservoir as a function of the initial effective stress of the core sample under reservoir conditions and a predetermined overburden stress of the reservoir.

In some implementations, determining the initial pore pressure of the reservoir includes first determining, by the system, the overburden stress of the reservoir as a function of i) depth of the core sample, ii) ground surface pressure, iii) gravitational acceleration, and iv) a density of overlying rock, and then determining, by the system, a difference between i) the initial effective stress of the core sample under reservoir conditions and ii) the overburden stress of the reservoir.

Implementations of the present disclosure include a system that includes at least one processing device and a memory communicatively coupled to the at least one processing device. The memory stores instructions which, when executed, cause the at least one processing device to perform operations including receiving, by the processing device, sensor feedback from one or more sensors of a core sample test assembly that includes a flow inlet and a flow outlet, the core sample test assembly containing a core sample obtained from a reservoir, and the receiving including receiving the sensors feedback while the core sample test assembly performs a permeability operation on the core sample by flowing a test fluid from the flow inlet, across the core sample, and out of the flow outlet. The operations also include determining, by the processing device and as a function of the sensor feedback, an effective stress acting on the core sample as the effective stress acting on the core sample increases. The operations also include determining, by the processing device, a natural logarithm of permeability of the core sample as a function of the effective stress. The operations also include determining, by the processing device and as a function of the natural logarithm of permeability of the core sample, an initial pore pressure of the reservoir.

In some implementations, the operations further include, before determining the initial pore pressure of the reservoir, determining, by the processing device and as a function of the natural logarithm of permeability of the core sample, an initial effective stress of the core sample, and determining the initial pore pressure of the reservoir includes determining, by the processing device and as a function of the initial effective stress of the core sample, the initial pore pressure of the reservoir.

In some implementations, the initial effective stress of the core sample is a point of effective stress at which a rate of change of the natural logarithm of permeability increases.

In some implementations, determining the initial effective stress of the core sample includes generating, by the processing device, an effective stress versus natural logarithm of permeability curve, and determining the initial effective stress of the core sample includes determining a point of effective stress in the graph in which a slope of the curve increases.

Particular implementations of the subject matter described in this specification can be implemented so as to realize one or more of the following advantages. For example, the system of the present disclosure enables the determination of the initial pore pressure of a reservoir without having to perform wellbore tests (e.g., diagnostic fracture injection tests), which can save time and resources. Additionally, the system of the present disclosure enables the determination of the initial pore pressure of a reservoir from a laboratory permeability test, which can increase the accuracy and reliability of the measurements.

BRIEF DESCRIPTION OF THE DRAWINGS

FIG. 5 is a flow chart of a method determining a property of a reservoir.

DETAILED DESCRIPTION OF THE DISCLOSURE

The present disclosure describes a core sample test system and method for determining the initial pore pressure of a reservoir (e.g., an unconventional reservoir). The core sample test system generates information from one or more tests performed on a core sample of the reservoir to quickly and reliably determine the initial pore pressure of a reservoir.

The initial pore pressure of a reservoir is an important parameter in oil and gas production. From initial pore pressure, one can determine various fluid properties of the production fluid, estimate the amount of hydrocarbons in place, predict an overall recovery factor from a well, and determine other parameters and characteristics of the well and reservoir. In some aspects, pore pressure refers to the pressure of the fluid (e.g., hydrocarbons) held within the pore space of the rock at a given depth.

Figure 1:
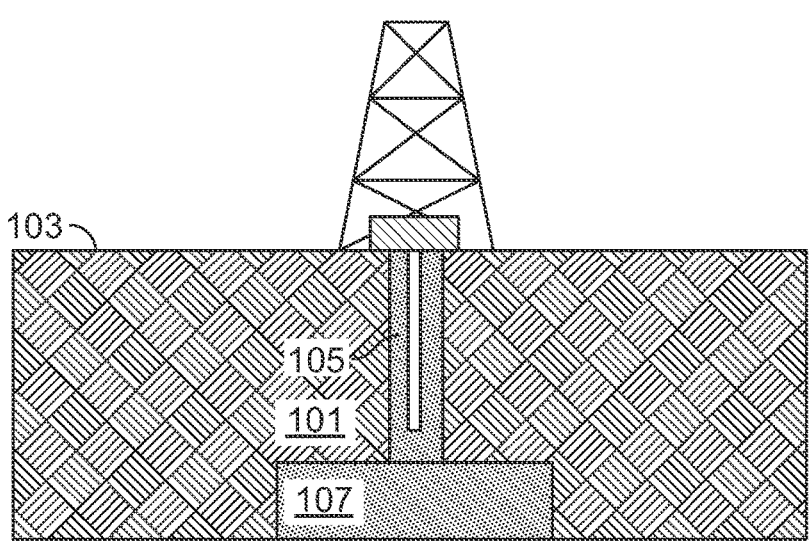
FIG. 1 shows a front, partial cross-sectional view of an example well system.

FIG. 1 shows a wellbore 105 (e.g., a production wellbore) that is used to produce trapped hydrocarbons from a reservoir 107 at a subterranean or geologic formation 101. The wellbore 105 extends through a subterranean zone that includes the geologic formation 101. For example, the wellbore 105 extends down from a surface 103 (e.g., a terranean surface) of the wellbore 105 and is formed in the geologic formation 101. As further describe in detail below with respect to FIGS. 2-4, a rock sample (e.g., a core sample) extracted from the hydrocarbon reservoir 107 can be tested to determine properties of the reservoir 107.

Figure 2:
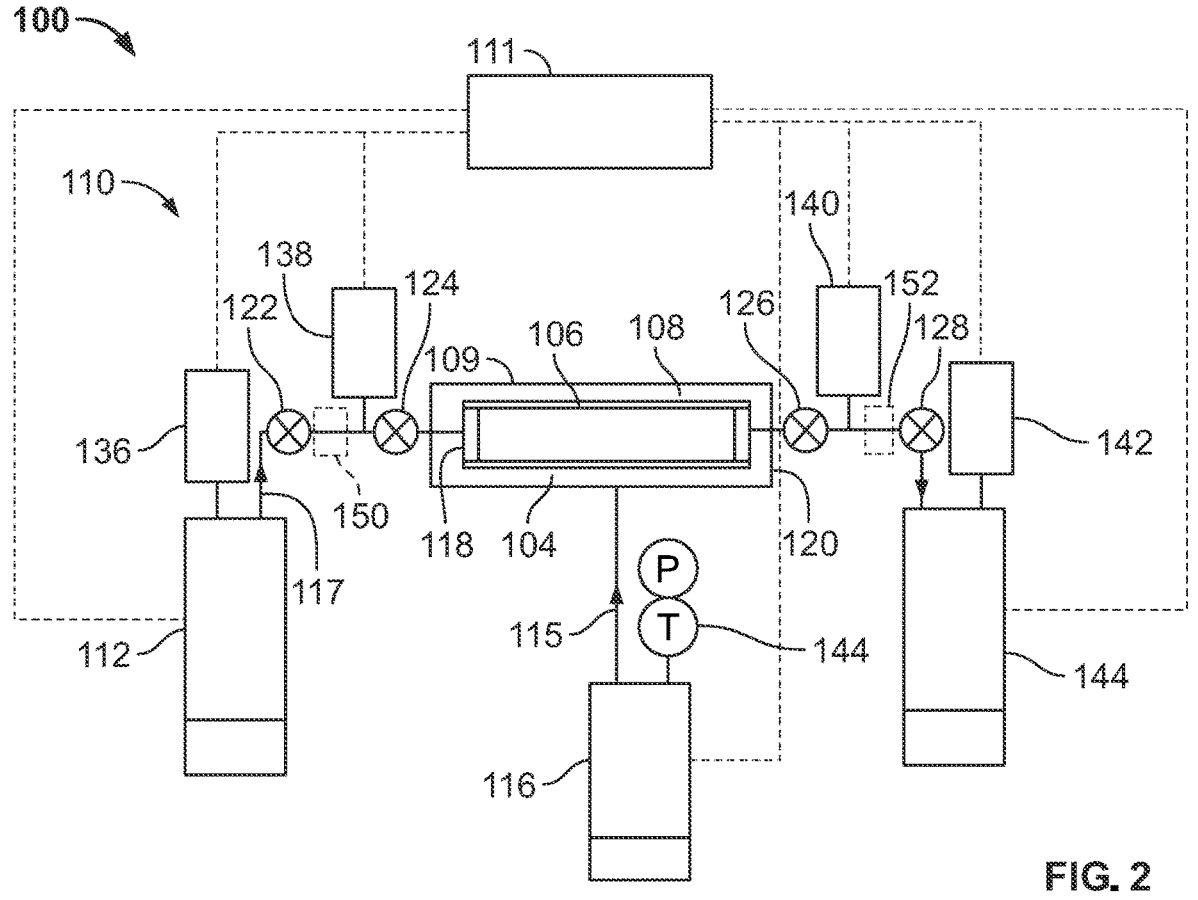
FIG. 2 shows a schematic diagram of an example core sample test system.

FIG. 2 shows a core sample test system 100 (e.g., a permeability measurement assembly) that includes a core sample assembly 110 and a controller 111 or control system. The core sample assembly 110 includes a housing or tank 109 in which a core sample 106 is placed and secured. The test system uses pumps 112, 116, 114 to move fluid and change the pressure of the fluids in and around the core sample 106 during the test.

The system 100 includes a sleeve 108 that encircles or wraps around the core sample 106 and prevents fluid inside the core sample from mixing with fluid in the tank 109. In some aspects, the core sample 106 is a cylindrical core sample with a diameter of between 1 to 3 inches and a length of between 1 and 5 inches. In some aspects, the rock sample 106 contains fresh or induced fractures.

In some aspects, prior to placing the core sample 106 within the core sample assembly 110, the core sample 106 is cut and pre-processed, e.g., to remove mobile water and hydrocarbon fluids therefrom. In some examples, the pre-processing includes trimming and polishing the end faces of the cylindrical core sample 106 such that the two end faces are parallel to each other and perpendicular to the longitudinal axis of the cylindrical core sample 106.

The core sample test system 100 is operated to determine one or more characteristics or properties of the core sample 106 that is positioned within the system 100. Such characteristics include, for example, permeability, pressure dependent characteristics, as well as poroelastic characteristics. In some aspects, the core sample 106 is a shale rock sample taken from a subterranean formation. Also, the core sample 106 can be a rock samples from conventional and unconventional reservoir.

The pumps include an upstream pump 112, a downstream pump 114, and a confining pump 116. The housing 109 is a pressurized container that defines a volume 104 in which the core sample 110 is placed. As shown in this example, the upstream pump 112 is fluidly coupled to a pressurized fluid inlet 118 at one end of the core sample and the downstream pump 114 is fluidly coupled to a pressurized fluid outlet 120 at an opposite end of the core sample 106. These pumps 112, 114 flow a test fluid 117 across the core sample 106 and change the pore pressure of the core sample 106.

The confining pump 116 is fluidly coupled to the housing 109 and is operable to circulate or flow a pressurized fluid 115 (e.g., a gas or other fluid) into the volume 104 to controllably change or maintain a pressure of the volume 104 (sometimes called a confining pressure). The differential stress acting on the core sample 106 is a function of the pore pressure and the confining pressure. For example, the differential stress is the difference between the pore pressure and the confining pressure, so that increasing the confining pressure while the pore pressure remains constant increases the differential stress.

In some aspects, the core sample test system 100 includes multiple sensors (or groups of sensors) 136, 138, 140, 142, 144 as well as valves 122, 124, 126, 128. Each of the fluid sensors 136, 138, 140, 142, 144 sense fluid characteristics of the fluid 115 such as pressure, temperature, or a combination thereof. In some aspects, each of the valves 122, 124, 126, 128 are operable to regulate a flow of fluids 115, 117 during the test. Each of the fluid sensors can be, for example, a high accuracy, high precision sensor. In some aspects, each sensor is capable of measuring both pressure and temperature simultaneously. The control system 111 uses the sensor feedback to control the valves and the pumps during the test to achieve desired testing conditions.

For example, the control system 111 (or controller) is communicably coupled to the fluid pumps 112, 114, 116 to control operation (e.g., speed,) of each fluid pump individually. The control system 111 is also communicably coupled to the fluid sensors 136, 138, 140, 142, 144 to receive sensor feedback (e.g., fluid pressure, fluid temperature, flow rate, or a combination thereof). The control system 111 controls, based on the sensor feedback, the pumps and valves to control the parameters of the fluids 115, 117 during the laboratory tests. Although not shown, additional components, such as valves (e.g., modulating or shut-off), power supplies, can also be included within the system 100 for operation. In some aspects, the experiment can be performed manually by an operator (manually controlling the operation of the pumps and valves) without the controller 111.

In some aspects, the control system 111 can be implemented as a distributed computer system disposed partly near the core sample test assembly 110 and partly at a remote location. The computer system can include one or more processors and a computer-readable medium storing instructions executable by the one or more processors to perform the operations described here. In some implementations, the controller 111 can be implemented as processing circuitry, firmware, software, or combinations of them.

To perform the permeability measurement on the core sample 106, an operator first positions the core sample 106 the container 109. Then, the test fluid is flowed from the inlet

118, across the core sample 106, and out of the flow outlet 120. The test fluid is used to change or maintain the pore pressure of the core sample at a desired level.

To prevent the test fluid from mixing with the confining pressure, the core sample 106 is enclosed by sleeve 108 around a radial surface of (in this example) the cylindrically shaped sample 106. In this example, axial faces of the core sample 106 are exposed to the flow inlet 118 and the flow outlet 120, respectively. The core sample 106 is positioned in the volume 104 of the pressurized container 102 and thus subjected to pressure by the pressurized fluid 115 in the pressurized container 109 and at the pressurized fluid inlet 118 and outlet 120. The test is performed while preventing fluid exchange between the pressurized gas 115 and the fluid 117 flowing through the sample from inlet 118 to outlet 120.

In some aspects, operation of the core sample test system 100 utilizes a steady state method, e.g., the pressure at a particular location in the core sample test system 100 does not appreciably change with time once in steady state.

In some aspects, the experimental setup scheme uses the pressure pulse decay (PPD) method. To do so, the core sample test assembly 110 has an upstream gas reservoir (e.g., a pressurized fluid reservoir) 150 disposed between the two valves 122, 124 at the inlet (and the two valves 122, 124 can be disposed upstream of inlet sensor 138) and a downstream gas reservoir (e.g., a pressurized fluid reservoir) 152 disposed between the two valves 126, 184 at the outlet (and the two valves 126, 184 can be disposed downstream of outlet sensor 140). During the PPD method, the working fluid 117, used for measuring permeability, is injected from the inlet and outlet of the rock sample with upstream and downstream pumps until the pore pressure within the rock sample equilibrates and reaches the desired initial value. Then, gas pressure pulse is created in the upstream gas reservoir 140 by injecting a certain amount of the working fluid 117.

Figure 3:
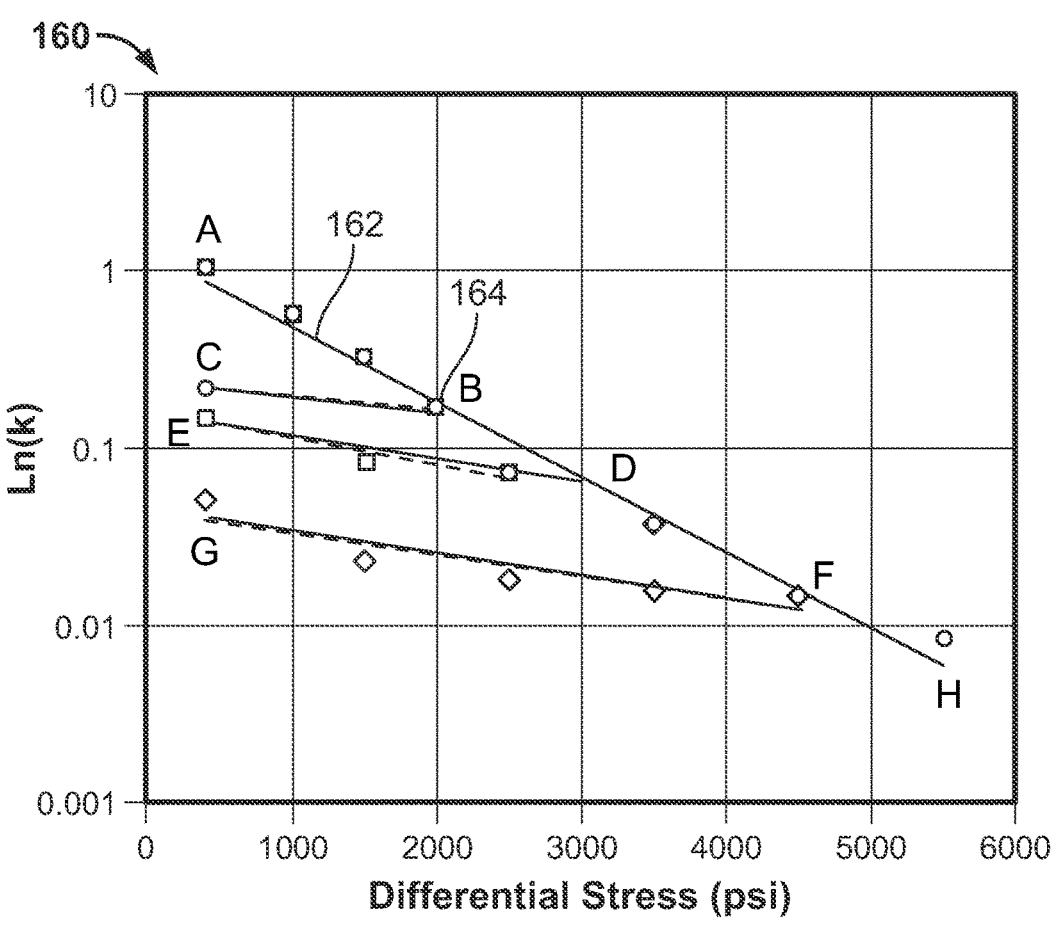
FIG. 3 shows a graph that shows core permeability measurements of the core sample under different loading and unloading conditions of the core sample.
Figure 4:
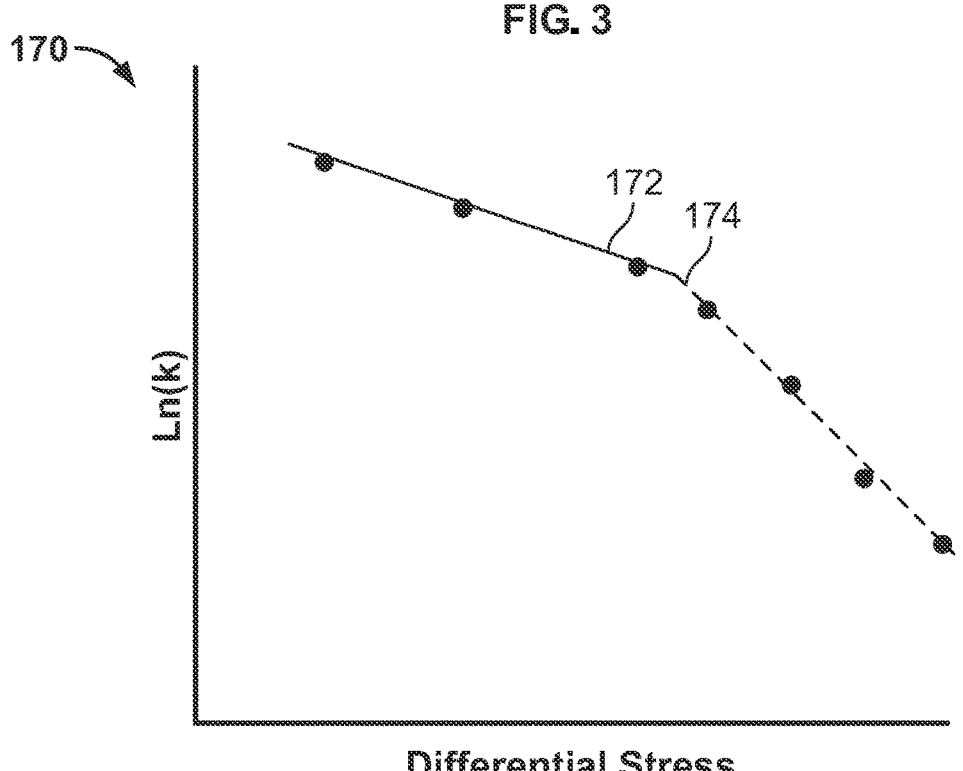
FIG. 4 shows a graph that describes a core sample property determined during an example method for testing a core sample according to the present disclosure.

Referring also to FIGS. 3 and 4, during or after the test, the control system 111 determines, as a function of the sensor feedback, the differential stress acting on the core sample 106 and the natural logarithm of permeability of the core sample 106.

Then, using the steady state method, permeability can be then estimated with Darcy's law expressed as:

$$Q = \frac{kA\rho}{\mu}\frac{\Delta p}{L}$$

where Q is mass flow rate, k is permeability, $\rho$ is fluid density, $\mu$ is fluid viscosity, $\Delta p$ is pressure difference between the inlet and outlet of the core sample 106, and A and L are the sample's cross-sectional area and length, respectively. Volumetric flow rates from the upstream pump and to the downstream pump are measured. The corresponding mass flow rates are determined by multiplying the volumetric flow rates with local fluid densities that depend on pressure and temperature.

FIG. 3 shows a graph generated during a permeability operation (e.g., permeability test) on the core sample as effective stress is increased and decreased. In some aspects, the effective stress is defined as a pressure differential between a pore pressure of the core sample and a confining pressure exerted on the core sample by the confining fluid. To increase the effective stress, the pressure of the confining fluid in the pressurized container can be increased while maintaining the pore pressure constant.

In some aspects, the core sample used in this test has natural, fresh, or induced fractures. The graph in FIG. 3 shows the principle from which one can determine initial effective stress by considering the stress history of the core sample and the results of permeability tests on the core sample.

As shown in FIG. 3, the test starts at point A and, under constant pore pressure (e.g., constant pore pressure of 2,500 psi), the confining pressure is increased to increase the effective stress on the core sample. The rock deformation is only determined by effective stress and its history. As the effective stress increase from point A to point B, the natural logarithm "ln(k)" of the permeability of the core sample, decreases at a substantially constant rate.

As the effective stress is decreased (e.g., during an unloading test) from point B to point C, the natural logarithm of permeability increases at a different rate of change than the rate of change from A to B. In other words, the natural logarithm of permeability changes along a line different than the A to B line although the effective stress is the same that the core sample experience in the loading test from point A to point B.

Then, the effective stress is increased again but more than previously, passing point B all the way to point D. It is observed that, from point C to point B, the natural logarithm of permeability essentially follows the same straight line as during the test from point B to point C. However, after point B, the natural logarithm of permeability continues the original straight line (decreases at the same rate as from point A to point B).

Notably, the slope of the curve changes where, for fresh or induced fractures, the loading test beyond point B is conducted under an effective stress that the rock sample has not previously experienced, as the core sample has only experienced the effective stress from point A to point B, from point B to point C, and from point C to point B. The same follows as the core sample is tested from points D to E, E to D, D to F, F to G, G to F, and F to H.

Thus, the rate of change of the natural logarithm of permeability within the effective stress that the core sample has previously experienced is different than the rate of change of the natural logarithm of permeability within effective stress that the core sample has not previously experienced. In other words, as shown in the graph 160 of FIG. 3, the differential stress vs. natural logarithm of permeability curve 162 has a first slope as the core sample is tested under effective stress previously experienced by the core sample, and then a second slope greater than the first slope as the core sample is tested under effective stress not previously experienced by the core sample.

Therefore, the turning point 164 in which the slope changes corresponds to the maximum effective stress that the rock has previously experienced. And thus, the turning point is said to be the initial effective stress of the core sample under reservoir conditions.

As shown in FIG. 4, as the laboratory permeability test or operation is performed on a core sample obtained from a reservoir, the control system 111 measures, during the operation, the differential stress (e.g., effective stress) as the differential stress increases. The core sample contains natural fractures. The controller determines the natural logarithm of permeability of the core sample as a function of the effective stress.

From the natural logarithm of permeability, an operator can quickly determine where the turning point 174 is. The turning point 174 corresponds to the initial effective stress of the core sample. From the initial effective stress, one can determine the initial pore pressure of the reservoir as a function of the initial effective stress of the core sample.

For example, the controller generates a graph 170 that includes a differential stress vs. natural logarithm of permeability curve 172. The curve 172 has the turning point 174 which corresponds to the initial pore pressure of the rock sample under reservoir conditions. Because the initial pore pressure of the reservoir is determined as the difference between overburden stress and initial effective stress (e.g., subtracting initial effective stress from overburden stress), the initial pore pressure can be quickly determined after determining the initial effective stress.

As shown in FIG. 4, the initial effective stress of the core sample is a point of effective stress at which a rate of change of the natural logarithm of permeability increases (e.g., the slope of the curve decreases). The initial effective stress can be determined from the graph 170 or directly from the natural logarithm of permeability data by determining the point at which the natural logarithm of permeability as a function of differential stress begins to decrease more rapidly. In some aspects, the rate of change is a rate that describes how one quantity changes in relation to another quantity. For example, the rate of change of the natural logarithm of permeability is with respect to the (i.e., as a function of) differential stress.

In some aspects, to make sure that the turning point 174 is plotted (e.g., included in the test), the loading test can begin a point of effective stress that has already been (or likely been) experienced by the rock sample with natural fractures (e.g., less than the initial effective stress of the core sample), such as 200 to 500 psi. Then, during the test, the graph 170 can be generated in real time (or near real time) so that the operator can know to what value of effective stress the core sample should be tested so that the graph 170 includes the turning point 174.

In some aspects, the initial effective stress represented by turning point 174 is the an initial effective stress of the core sample under reservoir conditions. Thus, determining the initial pore pressure of the reservoir includes determining the initial pore pressure of the reservoir as a function of the initial effective stress of the core sample with natural fractures under reservoir conditions and a predetermined overburden stress of the reservoir.

As shown in FIG. 2, evolutions of the gas pressures from the two gas reservoirs are monitored as a function of time. Using the PPD method, the permeability is determined by fitting the pressure data with the relevant analytical solution to fluid flow within the test system, with permeability being a fitting parameter. In some aspects, since fluid and rock properties could be approximated as constants, the governing equation for working fluid flow is linear and can be solved analytically. The solution allows the permeability to be related to pressures from the upstream and downstream reservoirs by the following equation:

$$\ln(p_u - p_d) = -fkt + C$$

where $p_u$ and $p_d$ are pressures at the upstream and downstream reservoirs, respectively. $f$ is a known function of geometry of the rock sample (length and cross-sectional area), rock porosity, and properties of the working fluid (density, viscosity and compressibility). Fitting the pressure data with the above equation gives the permeability value of the rock sample being tested for the given pore pressure and confining stress (or pressure).

The reservoir's initial pore pressure is determined by reservoir overburden stress minus the reservoir's initial effective stress. The following equation is used for this purpose:

$$P = P_0 + g \int_0^{Z^*} \rho(z) \, dz$$

where the overburden stress P at a depth Z* (which is zero at the ground surface) is a function of depth, ground-surface pressure $P_0$, gravitational acceleration g, and the density of the overlying rock $\rho$.

FIG. 5 shows a flow chart of a method (500) of determining initial pore pressure of a reservoir. The method includes performing, on a core sample (with natural fractures) obtained from a reservoir and positioned in a permeability measurement assembly that includes a flow inlet, a permeability operation on the core sample by flowing a test fluid from the flow inlet and into the core sample and changing an effective stress acting on the core sample (505). The method also includes determining a natural logarithm of permeability of the core sample as a function of the effective stress (510). The method also includes determining, as a function of the natural logarithm of permeability of the core sample, an initial pore pressure of the reservoir (515).

Figure 6:
FIG. 6 is a schematic illustration of an example controller (or control system) for a core sample test system according to the present disclosure.

FIG. 6 is a schematic illustration of an example control system or controller for a core sample test system according to the present disclosure. For example, the controller 600 may be, include, or be part of the controller 111 shown in FIG. 1. The controller 600 is intended to include various forms of digital computers, such as printed circuit boards (PCB), processors, digital circuitry, or otherwise. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 600 includes a processor 610, a memory 620, a storage device 630, and an input/output device 640. Each of the components 610, 620, 630, and 640 are interconnected using a system bus 650. The processor 610 is capable of processing instructions for execution within the controller 600. The processor may be designed using any of a number of architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the controller 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the controller 600. In one implementation, the storage device 630 is a computer-readable medium. In various different implementations, the storage device 630 may be a floppy disk device, a hard disk device, an optical disk device, or a tape device.

The input/output device 640 provides input/output operations for the controller 600. In one implementation, the input/output device 640 includes a keyboard and/or pointing device. In another implementation, the input/output device 640 includes a display unit for displaying graphical user interfaces.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

EXAMPLES

In an example implementation, a method includes performing, on a core sample obtained from a reservoir and positioned in a permeability measurement assembly that includes a flow inlet, a permeability operation by flowing a test fluid from the flow inlet and into the core sample and changing an effective stress acting on the core sample. The method also includes determining a natural logarithm of permeability of the core sample as a function of the effective stress, and determining, as a function of the natural logarithm of permeability of the core sample, an initial pore pressure of the reservoir.

In an example implementation combinable with any other example implementation, the method further includes, before determining the initial pore pressure of the reservoir, determining, as a function of the natural logarithm of permeability of the core sample, an initial effective stress of the core sample. Determining the initial pore pressure of the reservoir comprises determining, as a function of the initial effective stress of the core sample, the initial pore pressure of the reservoir.

In an example implementation combinable with any other example implementation, the initial effective stress of the core sample is a point of effective stress at which a rate of change of the natural logarithm of permeability increases.

In an example implementation combinable with any other example implementation, determining the initial effective stress of the core sample comprises generating a graph comprising an effective stress versus natural logarithm of permeability curve, and determining the initial effective stress of the core sample comprises determining a point of effective stress in the graph in which a slope of the curve increases.

In an example implementation combinable with any other example implementation, changing the effective stress comprises increasing the effective stress from a first value of effective stress that is less than the initial effective stress of the reservoir, to a value of effective stress that is greater than the initial effective stress of the reservoir.

In an example implementation combinable with any other example implementation, increasing the effective stress comprises increasing a pressure of a confining fluid residing within a pressurized container in which the core sample resides during the permeability operation.

In an example implementation combinable with any other example implementation, the initial effective stress of the reservoir is an initial effective stress of the core sample under reservoir conditions, and determining the initial pore pressure of the reservoir comprises determining the initial pore pressure of the reservoir and a predetermined overburden stress of the reservoir.

In an example implementation combinable with any other example implementation, determining the initial pore pressure of the reservoir comprises first determining the overburden stress of the reservoir as a function of i) depth of the core sample, ii) ground surface pressure, iii) gravitational acceleration, and iv) a density of overlying rock, and then subtracting the initial effective stress of the core sample under reservoir conditions from the overburden stress of the reservoir.

In an example implementation combinable with any other example implementation, performing the permeability operation comprises using at least one of a steady-state flow method or a pressure pulse decay method.

In an example implementation combinable with any other example implementation, the effective stress comprises a pressure differential between a pore pressure of the core sample and a confining pressure exerted on the core sample by a confining fluid, and increasing the effective stress comprises increasing the confining pressure while maintaining the pore pressure substantially constant.

In an example implementation, a method comprises receiving, by a system that comprises one or more computers in one or more locations, sensor feedback from one or more sensors of a core sample test assembly that comprises a flow inlet and a flow outlet, the core sample test assembly containing a core sample obtained from a reservoir, and the receiving comprising receiving the sensors feedback while the core sample test assembly performs a permeability operation on the core sample by flowing a test fluid from the flow inlet, across the core sample, and out of the flow outlet. The method also includes determining, by the system and as a function of the sensor feedback, an effective stress acting on the core sample as the effective stress acting on the core sample increases. The method also includes determining, by the system, a natural logarithm of permeability of the core sample as a function of the effective stress, and determining, by the system and as a function of the natural logarithm of permeability of the core sample, an initial pore pressure of the reservoir.

In an example implementation combinable with any other example implementation, the method further includes, before determining the initial pore pressure of the reservoir, determining, by the system and as a function of the natural logarithm of permeability of the core sample, an initial effective stress of the core sample. Determining the initial pore pressure of the reservoir comprises determining, by the system and as a function of the initial effective stress of the core sample, the initial pore pressure of the sample.

In an example implementation combinable with any other example implementation, the initial effective stress of the core sample is a point of effective stress at which a rate of change of the natural logarithm of permeability increases.

In an example implementation combinable with any other example implementation, determining the initial effective stress of the core sample comprises generating, by the system and on a user interface, a graph comprising an effective stress versus natural logarithm of permeability curve, and determining the initial effective stress of the core sample comprises determining a point of effective stress in the graph in which a slope of the curve increases.

In an example implementation combinable with any other example implementation, the initial effective stress of the core sample is an initial effective stress of the core sample under reservoir conditions, and determining the initial pore pressure of the reservoir comprises determining, by the system, the initial pore pressure of the reservoir as a function of the initial effective stress of the core sample under reservoir conditions and a predetermined overburden stress of the reservoir.

In an example implementation combinable with any other example implementation, determining the initial pore pressure of the reservoir comprises first determining, by the system, the overburden stress of the reservoir as a function of i) depth of the core sample, ii) ground surface pressure, iii) gravitational acceleration, and iv) a density of overlying rock, and then determining, by the system, a difference between i) the initial effective stress of the core sample under reservoir conditions and ii) the overburden stress of the reservoir.

In an example implementation, a system includes at least one processing device and a memory communicatively coupled to the at least one processing device. The memory stores instructions which, when executed, cause the at least one processing device to perform operations comprising receiving, by the processing device, sensor feedback from one or more sensors of a core sample test assembly that comprises a flow inlet and a flow outlet, the core sample test assembly containing a core sample obtained from a reservoir, and the receiving comprising receiving the sensors feedback while the core sample test assembly performs a permeability operation on the core sample by flowing a test fluid from the flow inlet, across the core sample, and out of the flow outlet. The operations also include determining, by the processing device and as a function of the sensor feedback, an effective stress acting on the core sample as the effective stress acting on the core sample increases. The operations also include determining, by the processing device, a natural logarithm of permeability of the core sample as a function of the effective stress. The operations also include determining, by the processing device and as a function of the natural logarithm of permeability of the core sample, an initial pore pressure of the reservoir.

In an example implementation combinable with any other example implementation, the operations further comprise, before determining the initial pore pressure of the reservoir, determining, by the processing device and as a function of the natural logarithm of permeability of the core sample, an initial effective stress of the core sample, and determining the initial pore pressure of the reservoir comprises determining, by the processing device and as a function of the initial effective stress of the core sample, the initial pore pressure of the reservoir.

In an example implementation combinable with any other example implementation, the initial effective stress of the core sample is a point of effective stress at which a rate of change of the natural logarithm of permeability increases.

In an example implementation combinable with any other example implementation, determining the initial effective stress of the core sample comprises generating, by the processing device, an effective stress versus natural logarithm of permeability curve, and determining the initial effective stress of the core sample comprises determining a point of effective stress in the graph in which a slope of the curve increases.

What is claimed is:

1. A method, comprising:
performing, on a core sample obtained from a reservoir and positioned in a permeability measurement assembly that includes a flow inlet, a permeability operation by flowing a test fluid from the flow inlet and into the core sample and changing an effective stress acting on the core sample;
determining a natural logarithm of permeability of the core sample as a function of the effective stress; and
determining, as a function of the natural logarithm of permeability of the core sample, an initial pore pressure of the reservoir.

2. The method of claim 1, further comprising:
before determining the initial pore pressure of the reservoir, determining, as a function of the natural logarithm of permeability of the core sample, an initial effective stress of the core sample; and
wherein determining the initial pore pressure of the reservoir comprises determining, as a function of the initial effective stress of the core sample, the initial pore pressure of the reservoir.

3. The method of claim 2, wherein the initial effective stress of the core sample is a point of effective stress at which a rate of change of the natural logarithm of permeability increases.

4. The method of claim 3, wherein determining the initial effective stress of the core sample comprises generating a graph comprising an effective stress versus natural logarithm of permeability curve, and determining the initial effective stress of the core sample comprises determining a point of effective stress in the graph in which a slope of the curve increases.

5. The method of claim 2, wherein changing the effective stress comprises increasing the effective stress from a first value of effective stress that is less than the initial effective stress of the reservoir, to a value of effective stress that is greater than the initial effective stress of the reservoir.

6. The method of claim 5, wherein increasing the effective stress comprises increasing a pressure of a confining fluid residing within a pressurized container in which the core sample resides during the permeability operation.

7. The method of claim 2, wherein the initial effective stress of the reservoir is an initial effective stress of the core sample under reservoir conditions, and determining the initial pore pressure of the reservoir comprises determining the initial pore pressure of the reservoir and a predetermined overburden stress of the reservoir.

8. The method of claim 7, wherein determining the initial pore pressure of the reservoir comprises first determining the overburden stress of the reservoir as a function of i) depth of the core sample, ii) ground surface pressure, iii) gravitational acceleration, and iv) a density of overlying rock, and then subtracting the initial effective stress of the core sample under reservoir conditions from the overburden stress of the reservoir.

9. The method of claim 1, wherein performing the permeability operation comprises using at least one of a steady-state flow method or a pressure pulse decay method.

10. The method of claim 1, wherein the effective stress comprises a pressure differential between a pore pressure of the core sample and a confining pressure exerted on the core sample by a confining fluid, and increasing the effective stress comprises increasing the confining pressure while maintaining the pore pressure substantially constant.

11. A method, comprising:
receiving, by a system comprising one or more computers in one or more locations, sensor feedback from one or more sensors of a core sample test assembly that comprises a flow inlet and a flow outlet, the core sample test assembly containing a core sample obtained from a reservoir, and the receiving comprising receiving the sensors feedback while the core sample test assembly performs a permeability operation on the core sample by flowing a test fluid from the flow inlet, across the core sample, and out of the flow outlet;
determining, by the system and as a function of the sensor feedback, an effective stress acting on the core sample as the effective stress acting on the core sample increases,
determining, by the system, a natural logarithm of permeability of the core sample as a function of the effective stress; and
determining, by the system and as a function of the natural logarithm of permeability of the core sample, an initial pore pressure of the reservoir.

12. The method of claim 11, further comprising:
before determining the initial pore pressure of the reservoir, determining, by the system and as a function of the natural logarithm of permeability of the core sample, an initial effective stress of the core sample; and
wherein determining the initial pore pressure of the reservoir comprises determining, by the system and as a function of the initial effective stress of the core sample, the initial pore pressure of the sample.

13. The method of claim 12, wherein the initial effective stress of the core sample is a point of effective stress at which a rate of change of the natural logarithm of permeability increases.

14. The method of claim 13, wherein determining the initial effective stress of the core sample comprises generating, by the system and on a user interface, a graph comprising an effective stress versus natural logarithm of permeability curve, and determining the initial effective stress of the core sample comprises determining a point of effective stress in the graph in which a slope of the curve increases.

15. The method of claim 12, wherein the initial effective stress of the core sample is an initial effective stress of the core sample under reservoir conditions, and determining the initial pore pressure of the reservoir comprises determining, by the system, the initial pore pressure of the reservoir as a function of the initial effective stress of the core sample under reservoir conditions and a predetermined overburden stress of the reservoir.

16. The method of claim 15, wherein determining the initial pore pressure of the reservoir comprises first determining, by the system, the overburden stress of the reservoir as a function of i) depth of the core sample, ii) ground surface pressure, iii) gravitational acceleration, and iv) a density of overlying rock, and then determining, by the system, a difference between i) the initial effective stress of the core sample under reservoir conditions and ii) the overburden stress of the reservoir.

17. A system, comprising:

at least one processing device; and a memory communicatively coupled to the at least one processing device, the memory storing instructions which, when executed, cause the at least one processing device to perform operations comprising:

receiving, by the processing device, sensor feedback from one or more sensors of a core sample test assembly that comprises a flow inlet and a flow outlet, the core sample test assembly containing a core sample obtained from a reservoir, and the receiving comprising receiving the sensors feedback while the core sample test assembly performs a permeability operation on the core sample by flowing a test fluid from the flow inlet, across the core sample, and out of the flow outlet;

determining, by the processing device and as a function of the sensor feedback, an effective stress acting on the core sample as the effective stress acting on the core sample increases, determining, by the processing device, a natural logarithm of permeability of the core sample as a function of the effective stress; and determining, by the processing device and as a function of the natural logarithm of permeability of the core sample, an initial pore pressure of the reservoir.

18. The system of claim 17, wherein the operations further comprise, before determining the initial pore pressure of the reservoir, determining, by the processing device and as a function of the natural logarithm of permeability of the core sample, an initial effective stress of the core sample, and wherein determining the initial pore pressure of the reservoir comprises determining, by the processing device and as a function of the initial effective stress of the core sample, the initial pore pressure of the reservoir.

19. The system of claim 18, wherein the initial effective stress of the core sample is a point of effective stress at which a rate of change of the natural logarithm of permeability increases.

20. The system of claim 17, wherein determining the initial effective stress of the core sample comprises generating, by the processing device, an effective stress versus natural logarithm of permeability curve, and determining the initial effective stress of the core sample comprises determining a point of effective stress in the graph in which a slope of the curve increases.

* * * * *